| United States Patent [19] | [11] Patent Number: 4,983,523 |
| Li et al. | [45] Date of Patent: Jan. 8, 1991 |

[54] METHODS FOR PREPARING SAMPLE NUCLEIC ACIDS FOR HYBRIDIZATION

[75] Inventors: May K. Li, Framingham; Donna McLaughlin, Hudson; Elaine Palome, Rowley; Jack Kessler, Ashland, all of Mass.

[73] Assignee: Gene-Trak Systems, Framingham, Mass.

[21] Appl. No.: 179,349

[22] Filed: Apr. 8, 1988

[51] Int. Cl.$^5$ .................. C12N 13/00; C12N 1/06; C12P 19/30

[52] U.S. Cl. ..................... 435/173; 435/89; 435/259; 435/803

[58] Field of Search ............. 435/173, 259, 803, 89

[56] References Cited

PUBLICATIONS

Derwent Abs. 87-313999/45 Gen. Probe AU8770404 (9-1987).
Derwent Abs. 83-769875/38 SU975020 (12-1982) Moskalenko et al.
Derwent Abs. 81-60507D/34 DD148447 (5-1987) Shishkov et al.
Biotech. Abs. 88-03296 DD243873 (3-1987) Akad.
Biotech Abs. 86-06167 "Enzyme Microbe Tech" (1986)8,4,192-204, Chisti.
Biotech. Abs. 82-04593 Biotechnol Lett(1982)4,653-54 Patel et al.
Derwent Abst. 88-163415/24 EP-271448 (6-1988) Ringrose.

*Primary Examiner*—Herbert J. Lilling
*Attorney, Agent, or Firm*—Mark A. Hofer

[57] ABSTRACT

A new method for releasing sample nucleic acids from cells, bacteria and viruses comprises non-invasively sonicating the sample contained within a sample container brought into physical contact with the vibrating element of a sonicator tuned to resonate at a frequency of 40 KHz or greater.

4 Claims, 1 Drawing Sheet

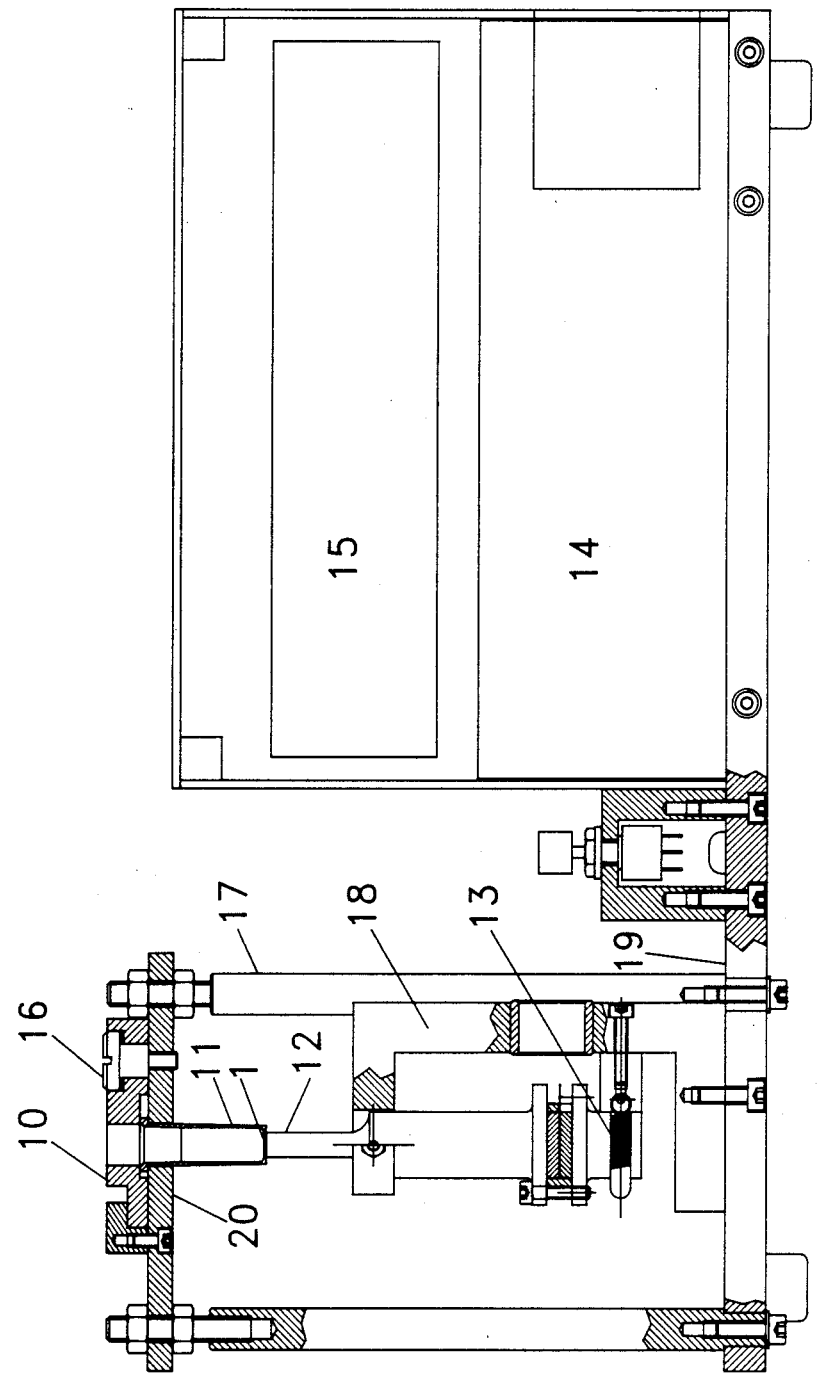

METHODS FOR PREPARING SAMPLE NUCLEIC ACIDS FOR HYBRIDIZATION

FIELD OF THE INVENTION

This invention relates generally to the field of nucleic acid hybridization and more specifically provides new methods for preparing biological samples for hybridization with nucleic acid probes.

BACKGROUND OF THE INVENTION

Nucleic acid probe hybridizations (DNA or RNA probe hybridizations) require biological samples to be processed to provide sample or target nucleic acid prior to hybridization with extrinsic nucleic acid probes. This processing is required because in order to hybridize the nucleic acid probes with complementary portions of the sample nucleic acids in turn contained within microorganisms defined as fungal cells, bacterial cells or viral particles, the sample nucleic acid must be released from inside the structure so as to be rendered accessible to the probes.

Nucleic acids have been traditionally released from biological systems via a variety of methods including the chemical action of detergents, bases, acids, chaotropes, organics and mixtures of these chemicals on samples. Various organisms, cells, bacteria or viruses characteristically require different chemical conditions in order to effectively release their nucleic acids. Physical methods of processing samples have also been practiced and include pressure, heat, freeze-thaw cycles and sonication with and without glass beads. Further, combinations of physical and chemical methods have also been used to prepare samples for DNA probe hybridizations such as chemical cell lysis followed by sonication.

Sonication devices employ ultrasonic vibrations and have previously been employed for a variety of processes including homogenization, cellular disruption, molecular disassociation, humidification, aerosol generation, lubrication, coating systems and instrument nebulizers. Ultrasound is commonly understood to encompass the propagation of a sound wave in a solution with the accompanying formation of regions of compression and rarefaction. The alternating acoustic pressure causes the making and breaking of microscopic bubbles. Pressure changes of 20,000 atmospheres can be achieved in cavitational microenvironments. The microscopic bubbles or cavities grow over many cycles and collapse with great force once they reach certain critical dimensions known as the critical bubble size. The critical bubble size is substantially a function of frequency; as frequency is increased, more power is required in order to produce cavitation. Above 1 MHz, the intensity of sonication is greatly diminished and cavitation cannot be produced at all above 2.5 MHz.

A number of different sonicators which cause cavitation have been used in studies involving nucleic acids including systems offered commercially by Heat Systems Ultrasonics, Tomy Co., Rapidis, Raytheon, Mullard and Branson. These commercial sonicators have traditionally been designed to resonate at a frequency between 5 and 35 KHz and most resonate at approximately 20 KHz. The typical commercially available sonicator has been used in one of two modes: (1) direct immersion of the vibrating probe into the sample, and (2) placement of both the container holding the sample and the vibrating transducer of the sonication unit into a common liquid or bath. The first mode disadvantageously incurs sample-to-sample carry-over and thus is not practical in a clinical setting. In the second mode of use, the liquid acts to couple the sonic vibrations to the sample in the container or cuvette and may also assist in cooling and/or controlling the sample temperature. While this method is relatively efficient, it is disadvantageously complicated by the necessary mechanics of the liquid bath and the contamination threat posed thereby. Accordingly its application in the clinical environment is also limited.

It is an object of the present invention to provide a new sonication system having an effectiveness comparable to the liquid bath sonication method.

It is another object of the present invention to provide a new sonication method for preparing samples for DNA probe hybridization which avoids the contamination disadvantages associated with immersion type sonication.

It is known that when a conventional ultrasonic transducer is applied directly to the surface of a container, ultrasonic energy is not readily transmitted to a liquid contained within the container. This occurs because a significant percentage of the energy is lost in the form of heat, either in the contact surfaces of the transducer and the container wall, or in the container material itself. The amount of energy actually transmitted is further limited by the acoustic impedances of each material. Thus, only a relatively small amount of the initial energy is actually transmitted to the liquid and cavitation fails to occur unless a very large excess of initial energy is applied. Application of such an excess of energy is generally highly disadvantageous because such results in highly localized heating often to the extent that melting of the container may occur. Such a result is quite clearly unacceptable, particularly in a clinical environment where samples may be dangerously infective.

It is yet another object of the present invention to provide a new method for preparing samples for DNA hybridization which utilize direct transducer - container contact while avoiding the application of previously required high levels of energy.

BRIEF DESCRIPTION OF THE DRAWINGS

These and other objects of the present invention will become clear upon examination of the drawing wherein the:

Figure shows a cross-sectional view of the most preferred embodiment of the non-invasive sonication device of the present invention.

SUMMARY OF THE INVENTION

In accordance with the principles and objects of the present invention there is provided a new method for preparing samples for nucleic acid hybridization with nucleic acid probes comprising providing the fluid sample containing the nucleic acid to be tested in a container, contacting the outside of the container with the vibrating element of a transducer device and energizing the sonicator for a predetermined period of time. Ideally that time period may range from about ten seconds to less than about ten minutes. It was surprisingly discovered that the foregoing method is approximately as effective as the immersion sonication procedures when the sonication device is tuned to resonate at between about 40 to about 100 KHz, most preferably around 60 KHz.

DETAILED DESCRIPTION AND BEST MODE

The most preferred embodiment of the present invention is depicted in the figure wherein an ultrasonic transducer 12 resonating above 40KHz is mounted on frame member 18 in turn mounted upon base 19 within housing 17. The ultrasonic transducer 12 is mounted upon pneumatic cylinder 13 for controlling the force of the ultrasonic tip 1 against disposable cuvette 11. Cuvette 11 is maintained against tip 1 by force retainer 10 which pivots at screw attachment site 16 to slidably engage the top of cuvette 11. Transducer 12 is controlled by frequency generator 15 and power supply 14 through electrical connections not shown.

In general, the preferred method of the instant invention comprises contacting a sample of bacteria, cells, viruses or other materials containing the nucleic acids to be assayed in a suitable solvent, most preferably a buffered solution of chaotropic agents to form a solution, a predetermined volume of which is added to a sample cuvette, typically injection molded in nature. Alternatively, the mixture may be formed within the cuvette in the first instance. The sample cuvette is then placed within mounting bracket 20 such that the bottom thereof comes into contact with the tip 1 of transducer 12. Force retainer 10 is pivotted to slidably engage the cuvette and retain the cuvette 11 within mounting bracket 20 whereby a predetermined pressure of approximately 8 to 30 pounds per square inch is maintained at the surface contact area between tip 1 and cuvette 11. Alternatively, the force retainer can apply the equivalent of approximately 10 pounds of weight as a retaining force. Such pressure may be most advantageously obtained by energizing pneumatic cylinder 13 to urge tip 1 against the bottom of cuvette 11 with the predetermined force. The sonicator 12 is then energized for a period of time generally greater than ten seconds and less than ten minutes, most preferably from one to five minutes. Most preferably the container will be one having a surface continuity on the inside surface of the wall in contact with or adjacent to the sonicator tip 1. Such discontinuities have been described in Swiss Patent Application No. 4,931/86-4, entitled "Sonication Device", and incorporated herein by reference, as enhancing the effectiveness of transmitted ultrasonic energy.

The non-invasive sonication method of the present invention is suitable for use with blood, urine, serum, cerebral spinal fluid, swabs, extracts from swabs and other types of fluid suspensions which require the release nucleic acids into solution. Most preferably, a duty cycle is imposed on the non-invasive sonicator 12 to allow heat dissipation at the surface of the tip 1 and the bottom of cuvette 11. The most preferred duty cycle (e.g., time of positive action per total time expressed in percent) is from about 25% to about 75%. Similarly, the most preferred embodiment of the sonication device of the present invention will be tuned to resonate at frequency of approximately 60 KHz.

Further understanding of the principles of the present invention may be had by studying the accompanying examples.

EXAMPLE 1

Pelleted cells from one ml aliquots of an overnight culture of Listeria innocua in a solvent of 2.5 M guanidinium thiocyanate at pH 7.5, which was 0.040M with respect to Tris-Cl and 0.010M with respect to ethylenediaminetetraacetate was subjected to probe immersion sonication, non-invasive sonication, and enzymatic treatment for comparison for determining the amount of hybridizable RNA released by each type of treatment. The hybridization assay employed was based upon measuring the ability of RNAse to degrade a non-hybridized single stranded radiolabeled RNA. The radiolabeled RNA (riboprobe) used in this assay was a 700 base sequence from the 3' end of the *E. coli* 16s ribosome cloned into an SP6 pGEM vector. SP6 RNA polymerase was used with $^{32}P$ labeled GTP to make RNA transcripts, i.e., riboprobe. Each sample was incubated with 1 ng of riboprobe for 15 minutes at 37° C. in 2.5M guanidinium thiocyanate at pH 7.5, which was 0.040M with respect to Tris-Cl and 0.010 M with respect to ethylenediaminetetraacetate. Each sample was diluted 20 fold into a 0.01 M Tris-Cl solution at pH 7.5 containing 0.2 mg/ml of ribonuclease and incubated at 45° C. for 15 minutes. Quantitation of hybridizable nucleic acid released was determined via precipitation of the surviving hybrids with trichloroacetic acid and scintillation counting.

Equal amounts of the overnight culture of Listeria innocua were subjected to (i) probe immersion sonication using a Heat Systems Ultrasonics' Model H-225, and (ii) a biochemical treatment comprising contact with an enzyme solution containing 5 units/$\mu$l amounts of mutanolysin and 10 mg/ml amounts of lysozyme. The ability of the probe immersion sohication and of the biochemical treatment for the release of hybridizable nucleic acid from Listeria innocua was compared to the non-invasive sonication employing the preferred sonicator depicted in the Figure. All other parameters of experimental protocol were identical. The Heat Systems Ultrasonics' W-225 was run at power level 5 with the microtip horn for four minutes at a duty cycle of 50%. The non-invasive sonicator was run at a duty cycle of 33% for six minutes. Non-invasive sonication proved to be as effective in releasing hybridizable targets as probe immersion sonication as depicted in the following table.

| Femptograms of *Listeria innocua* 16s RNA Hybridized | | | | |
|---|---|---|---|---|
| Trial No. | 1 | 2 | 3 | 4 |
| Biochemical Treatment | 5.69 | 5.36 | .387 | 4.30 |
| Probe Immersion Sonication | 3.81 | 5.23 | .534 | 2.25 |
| Non-Invasive Sonication | 4.2 | 4.80 | .413 | 4.15 |

EXAMPLE 2

A 1 ml cell pellate of Listeria innocua cultured overnight in broth was treated with 0.50 ml of the same mutanolysin and lysozyme enzyme solution and then suspended in 1.0 ml of 2.5M guanidine thiocyanate buffer. An equivalent volume of Listeria innocua was spun down and the Listeria innocua resuspended in 1.0 ml freshly drawn human blood which was subsequently treated by probe immersion sonication and non-invasive sonication for comparison. The non-invasive sonicator of the present invention and the Model H-225 from Heat Systems ultrasonics using microptips and a power setting of 4 were both set for a 33% duty cycle.

The amount of hybridizable nucleic acids released was determined using a $^{32}P$-labeled riboprobe (label probe) and an unlabeled capture probe. The label probe used was an RNA transcript sequence from the 5' end of the *E. coli* 16s ribosome cloned into a T7 pGEM vector.

T7 RNA polymerase was used with $^{32}P$ labeled GTP to make riboprobe. The capture probe consisted of a 44mer DNA oligo 5' TGTCCCCGAAGG-GAAAGCTCTGTCTCCAGAGTGGT-CAAAGATAT 3' which was tailed using terminal deoxy nucleotidyl transferase with approximately 160 deoxyadenine groups.

The capture probe and label probe were mixed with blood spiked with Listeria innocua as above and added to magnetic particles having dT14 covalently coupled to their surface, and incubated at room temperature for five minutes. Hybrids formed between the capture probe, label probe, and target nucleic acids were captured on the dT14 magnetic particles and separated from the assay mixture using a magnetic field. The magnetic particles were washed to remove non-specifically bound material and resuspended in a wash buffer containing 0.5% detergent and 0.5% BSA and heated to 68° C. for two minutes. The magnetic particles were then separated from the assay mixture using a magnetic field and discarded; the bulk solution was added to a second volume of fresh beads and the process repeated. The resultant bulk solution was added to scintillation cocktail and counted in a scintillation counter. The assay was run in triplicate for the non-invasive sonication and quadruplicate for the probe immersion sonication system. 50 ul aliquots were withdrawn from each sonication at one, two and three minutes and subjected to the hybridization assay. The amount of released hybridizable nucleic acid from each sonication treatment was compared to that released by the mutanolysin/lysozyme treatment (control). Results are depicted in the following table. At each time point the amount of hybridizable nucleic acid available for hybridization after non-invasive sonication was equal to or greater than that available with direct probe immersion sonication.

TABLE

EXAMPLE 2

Average Percent Release Relative to Mutanolysin/Lysozyme Treatment

| Method | 1 Minute | 2 Minutes | 3 Minutes |
|---|---|---|---|
| Non-invasive Solution | 32.5 | 52 | 48.5 |
| Invasive Solution | 9.9 | 16.9 | 23.3 |

EXAMPLE 3

The procedures set forth in Example 2 were repeated for purposes of comparing the non-invasive sonication with probe immersion sonication using the Model W-225 from Heat Systems ultrasonics at a power setting of 3 and a power setting of 5 in aliquots withdrawn from each sonication at one, two, three, four and five minute intervals and subjected to the same hybridization assay procedure. As the table below shows, at each time point, the amount of hybridizable nucleic acid available for hybridzation after non-invasive sonication was equal to or greater than that available with direct probe immersion sonication.

TABLE

EXAMPLE 3

Average Percent Release Relative to Mutanolysin/Lysozyme Treatment

| Method | 1 Min | 2 Min | 3 Min | 4 Min | 5 Min |
|---|---|---|---|---|---|
| Non-invasive Solution | 1.3 | 24.8 | 32.0 | 15.9 | 31.2 |
| Invasive Solution | | | | | |
| Power Output 5 | 1.0 | 6.0 | 12.0 | 8.6 | 21.0 |
| Power Output 3 | 1.2 | 3.9 | 5.3 | 5.0 | 7.0 |

What is claimed is:

1. A method for treating an aqueous sample containing microorganisms for releasing sample nucleic acids contained within the microorganisms for hybridization comprising the steps of:
   (a) providing a non-invasive sonicator having a vibrating element tuned to resonate at a frequency of at least of 40 KHz but less than 100 KHz;
   (b) further providing a container for receiving said aqueous sample, said container having at least one mating surface adapted for engaging with said vibrating element;
   (c) adding said aqueous sample to said container;
   (d) bringing said mating surface of said container into contact with said vibrating element of said sonicator while avoiding immersion of said vibrating element in said aqueous sample;
   (e) energizing said sonicator to cause said vibrating element to vibrate for a time period of at least about 10 seconds.

2. The method as provided in claim 1 wherein said container through said mating surface is brought into contact with said vibrating element sonicator with a force of at least about 8 pounds per square inch to about 30 pounds per square inch.

3. The method as provided in claim 1 where said sonicator is tuned to a frequency of about 60 KHz.

4. The method as provided in claim 3 wherein said sonicator has a positive duty cycle of between about 25% to about 75% and said energizing step occurs from about 30 seconds to about 5 minutes.

* * * * *